United States Patent [19]

Walsh

[11] 4,046,885

[45] Sept. 6, 1977

[54] METHOXY-SUBSTITUTED CYANOPHENYL ESTER DERIVATIVES OF PHOSPHORUS ACIDS AS INSECTICIDAL AGENTS

[75] Inventor: Edward N. Walsh, New City, N.Y.

[73] Assignee: Stauffer Chemical Company, Westport, Conn.

[21] Appl. No.: 688,506

[22] Filed: May 20, 1976

Related U.S. Application Data

[60] Division of Ser. No. 632,523, April 21, 1967, Pat. No. 3,983,188, which is a continuation-in-part of Ser. No. 328,463, Dec. 6, 1963, abandoned.

[51] Int. Cl.² ............................................. A01N 9/36
[52] U.S. Cl. .................................................... 424/210
[58] Field of Search ........................................ 424/210

[56] References Cited

U.S. PATENT DOCUMENTS

| | | | |
|---|---|---|---|
| 3,164,623 | 1/1965 | Schrader | 260/940 |
| 3,301,749 | 1/1967 | Sakai et al. | 260/940 X |

Primary Examiner—Allen J. Robinson
Attorney, Agent, or Firm—Charles B. Rodman; Roger S. Benjamin

[57] ABSTRACT

Methoxy-substituted cyanophenyl ester derivatives of phosphinic, phosphonic, phosphoric, thiophosphinic, thiophosphonic, and thiophosphoric acids having the general formula:

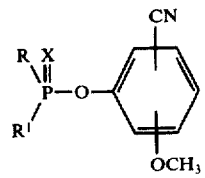

wherein R and R$^1$ are independently selected from the group consisting of lower alkyl, chloro-substituted lower alkyl, lower alkoxy, phenyl, phenoxy and lower dialkylamide, and X is oxygen or sulfur. The compounds are effective pesticides especially in the control of houseflies, American cockroach, milkweed bug and two-spotted mite. Representative compounds are O-ethyl-O-(2-methoxy-4-cyanophenyl) ethyl phosphonothioate and O,O-dimethyl-O-(2-methoxy-4-cyanophenyl) phosphorothioate.

7 Claims, No Drawings

METHOXY-SUBSTITUTED CYANOPHENYL ESTER DERIVATIVES OF PHOSPHORUS ACIDS AS INSECTICIDAL AGENTS

This application is a division of application Ser. No. 632,523, filed Apr. 21, 1967 and now U.S. Pat. No. 3,983,188, which was a continuation-in-part of application Ser. No. 328,463, filed Dec. 6, 1963, and now abandoned.

This invention is directed to certain novel phosphorus-containing compounds, a process for preparing said compounds, and their method of use as pest-controlling agents.

The novel compounds are the methoxy-substituted cyanophenyl ester derivatives of phosphinic, phosphonic, phosphoric, thiophosphinic, thiophosphonic, and thiophosphoric acids, which compound may be represented generically by the following general formula:

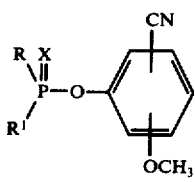

wherein R and R¹ are independently selected from the group consisting of lower alkyl, chloro-substituted lower alkyl, lower alkoxy, phenyl, phenoxy, and lower dialkylamide, and X is selected from the group consisting of oxygen and sulfur. The lower alkyl, chloro-substituted lower alkyl, and lower alkoxy groups represented by R and R¹, will contain up to 8 carbon atoms, either in branched or straight chains. The alkyl portions of the dialkylamido radicals will contain from 1 to 3 carbon atoms.

The novel compounds of the present invention are prepared according to the following general reaction:

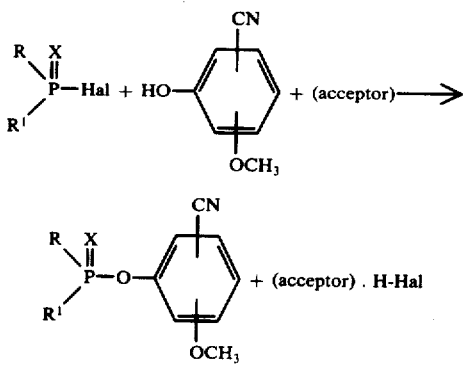

wherein Hal stand for a halogen selected from chlorine, iodine, and bromine, preferably chlorine, "acceptor" stands for a hydrogen halide acceptor such as a tertiary amine or the like, and R, R¹, and K are as defined hereinbefore. Reaction is preferably carried out at or slightly above room temperature, for example, at a temperature between about 20° and 80° C., although the reaction is possible at all temperatures between about 0° and 100° C. The hydrogen halide acceptor is useful in preventing possible side reactions between the product and the halogen acid generated in the reaction. In a preferred process for making the novel compounds of the invention, the reaction is preferably carried out in the presence of an inert organic solvent such as benzene, dioxime, toluene, and xylene. By a variation of the process, sodium carbonate, or the like, may be used in place of the hydrogen halide acceptor to remove acid from the reaction matrix.

The preparation of the compounds of this invention is illustrated by the following non-limiting examples, many variations of which will occur to those skilled in the art without departing from the spirit or scope thereof:

EXAMPLE 1

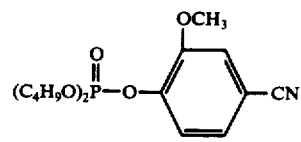

To 7.5 grams of vanillin nitrile, 6.0 grams of triethylamine and 75 ml. benzene maintained at a temperature of 20°–30° C. was added 11.4 grams of $(C_4H_9(O)_2P(O)Cl$. The reaction matrix was allowed to stir for 48 hours, after which time it was filtered and the filtrate was washed. The filtrate was then concentrated by evaporation to 60° C. at 1 mm. Hg to yield 12.6 grams (72% of theoretical yield) of 0,0-dibutyl-0-(2-methoxy-4-cyanophenyl) phosphate, having an index of refraction $N_D^{25} = 1.5331$.

EXAMPLE 2

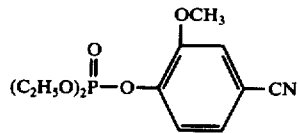

To 8.7 grams of $(C_2H_5O)_2P(O)Cl$ and 20 ml. of benzene was added dropwise, at 25° C., 7.5 grams of vanillin nitrile and 6.0 grams of triethylamine and 75 ml. of benzene. After stirring overnight at room temperature, the reaction mixture was heated to 60° C. for 1 hour, cooled, filtered, and the filtrate was concentrated by evaporation to 60° C. at 1 mm. Hg. The concentrate consisted of 14.0 grams (97% of theoretical yield) of 0,0-diethyl-0-(2-methoxy-4-cyanophenyl) phosphate, having an index of refraction $N_D^{25} = 1.4991$. By analysis, the product consisted of 10.9% P, 4.1% N, and 0.3% Cl, compared to the theoretical values of 10.9% P, 4.1% N, and 0.0% Cl for the compound of the formula shown immediately above.

EXAMPLE 3

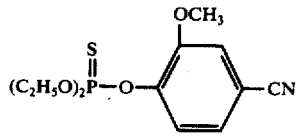

To 5.0 grams of vanillin nitrile and 3.7 grams of triethylamine in 75 ml. of benzene was added 6.3 grams of $(C_2H_5O)_2P(S)Cl$ and 20 ml. of benzene, while maintaining the reaction temperature between 25° and 35° C. The reaction matrix was allowed to stir for 1 hour at room temperature, after which it was heated to 65° ±

5° C. for 2 hours. This reaction was followed by cooling, filtration, and concentration of the filter cake by evaporation to 60° C. at 1 mm. Hg. to yield 6.5 grams (65% of theoretical yield) of 0,0-diethyl-0-(2-methoxy-4-cyanophenyl) phosphorothioate having an index of refraction $N_D^{25} = 1.5208$. By analysis, the product was found to contain 10.1% P, 11.3% S, and 3.5% N, compared to the theoretical values of 10.3% P, 10.6% S, and 4.65% N.

EXAMPLE 4

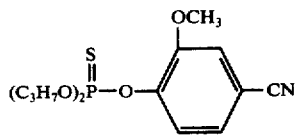

Using the procedure described in the foregoing example, and analogous starting materials, a 99% yield of 0,0-n-propyl-0-(2-methoxy-4-cyanophenyl) phosphorothioate having an index of refraction $N_D^{25} = 1.5168$ was prepared. This product analyzed as 9.1% P, 9.3% S, and 4.1% N, as compared to the theoretical values of 9.4% P, 9.7% S, and 4.25% N.

EXAMPLE 5

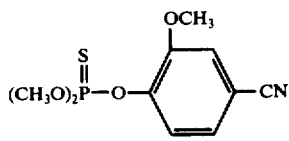

To 6.0 grams of $Na_2CO_3$ and 7.5 grams of vanillin nitrile in acetone was added 8.0 grams of $(CH_3O)_2P(S)Cl$. The reaction mixture was warmed to reflux temperature for 5 hours, cooled, and then poured into 250 cc. of ice water. The solids were then recovered, filtered and dried to yield 9.3 grams (68% of theoretical yield) of 0,0-dimethyl-0-(2-methoxy-4-cyanophenyl) phosphorothioate. This product was found to have a melting point at 70°-75° C. and an analysis of 9.8% P, 10.3% S, and 5.5% N, compared to 11.4% P, 11.7% S, and 5.1% N, theoretical.

EXAMPLE 6

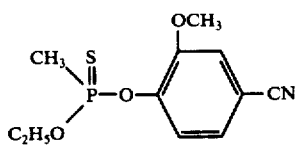

To 7.5 grams of vanillin nitrile and 6.0 grams of triethylamine in 50 ml. of benzene was added 7.4 grams of $(CH_3)(C_2H_5O)P(S)Cl$ in 10 ml. of benzene at 30° to 35° C. The reaction mixture was allowed to stir for 1 hour longer and then heated for an additional hour at 60° C., after which it was cooled and added to 100 cc. of water to dissolve the triethylamine hydrochloride. The organic fraction was transferred to a separatory funnel and washed with 50 ml. of 2% NaCH and 50 ml. of water. The aqueous phase was then counter-washed with 50 cc. of benzene. The benzene wash and the product were combined and concentrated by evaporation at 70° C. at 2 mm. Hg to yield 12.0 grams of solids having a melting point of 95°-100° C. The solid product was analyzed and found to be 0-ethyl-0-(2-methoxy-4-cyanophenyl) methylphosphonothioate, having an elemental composition of 10.9% P, 10.7% S, and 5.2% N, compared to 11.4% P, 11.8% S, and 5.2% N, theoretical.

Using a procedure substantially in accordance with those described in the foregoing examples, the following specific compounds were prepared:

EXAMPLE 7

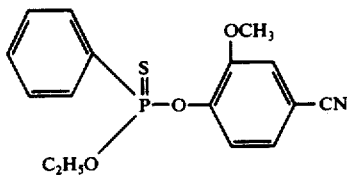

0-ethyl-0-(2-methoxy-4-cyanophenyl) phenylphosphonothioate.

Analysis — Found: 9.1% P; 10.0% S; 4.0% N. Calcd: 9.3% P; 9.6% S; 4.2% N.

Yield = 63% of theory

EXAMPLE 8

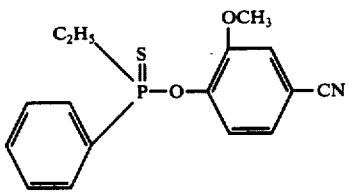

0-(2-methoxy-4-cyanophenyl) ethylphenylphosphinothioate.

Analysis — Found: 9.8% P; 10.3% S; 4.0% N. Calcd: 9.8% P; 10.1% S; 4.4% N.

Yield = 85% of theory

EXAMPLE 9

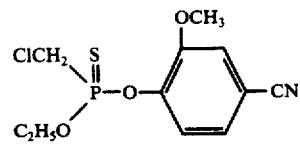

0-ethyl-0-(2-methoxy-4-cyanophenyl) chloromethylphsophonothioate

Analysis — Found: 10.0% P; 10.4% S; 7.7% Cl; 4.1% N. Calcd: 10.2% P; 10.5% S; 11.6% Cl; 4.6% N.

EXAMPLE 10

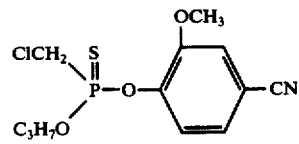

0-propyl-0-(2-methoxy-4-cyanophenyl) chloromethylphosphonothioate

Analysis — Found: 9.3% P; 9.8% S; 12.2% Cl; 4.5% N. Calcd: 9.7% P; 10.0% S; 11.1% Cl; 4.4% N.

Yield = 84.0% of theory

EXAMPLE 11

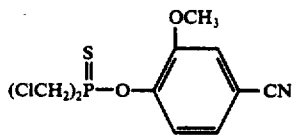

0-(2-methoxy-4-cyanophenyl) dichloromethylphosphinothioate
Yield = 95% of theory

EXAMPLE 12

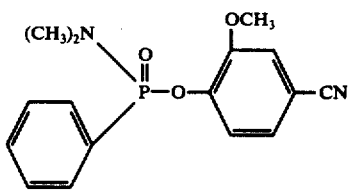

0-(2-methoxy-4-cyanophenyl)-N,N-dimethyl phenylphosphonamidate
Analysis — Found: 9.4% P; 8.6% N. Calcd: 9.8% P; 8.9% N.
Yield = 95.0% of theory

EXAMPLE 13

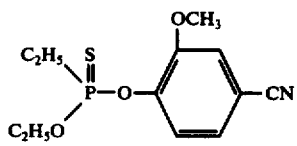

0-ethyl-0-(2-methoxy-4-cyanophenyl) ethyl phosphonothioate. Melting point 74.5° 76.5° C.
Analysis — Found: 10.80% P; 11.34% S; 4.89% N. Calcd: 10.88% P; 11.23% S; 4.91% N.
Yield = 70% of theory.

EXAMPLE 14

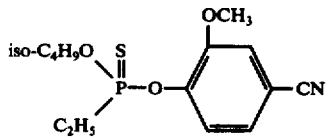

0-isobutoxy-0-(2-methoxy-4-cyanophenyl) ethyl phosphonothioate.

EXAMPLE 15

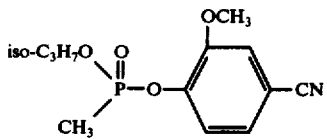

0-isopropyl-0-(2-methoxy-4-cyanophenyl) methyl phosphonothioate.

The following related compounds can also be prepared by reactions similar to those shown in Examples 1 through 6, using the corresponding reactants:

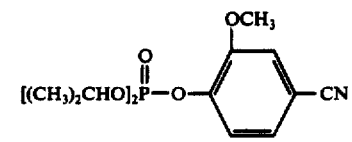

0,0di-i-propyl-0-(2-methoxy-4-cyanophenyl) phosphate

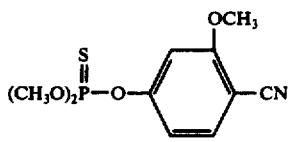

0,0-dimethyl-0-(3-methoxy-4-cyanophenyl) phosphorothioate

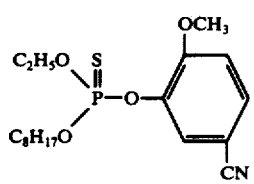

0-ethyl-0-octyl-0-(2-methoxy-5-cyanophenyl) phosphorothioate

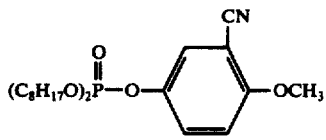

0,0-dioctyl-0-(3-cyano-4-methoxyphenyl) phosphate

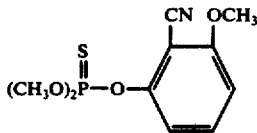

0,0-dimethyl-0-(2-cyano-3-methoxyphenyl) phosphorothioate

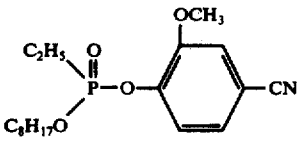

0-octyl-0-(2-methoxy-4-cyanophenyl) ethylphosphonate

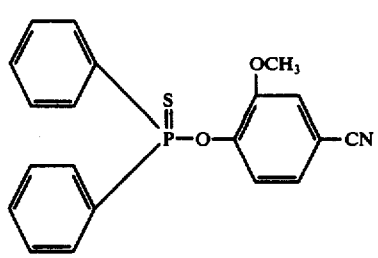

O-(2-methoxy-4-cyanophenyl) diphenyl phosphinothioate

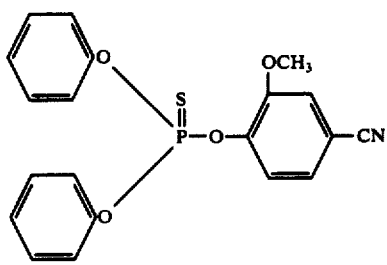

0,0-diphenyl-O-(2-methoxy-4cyanophenyl) phosphorothioate

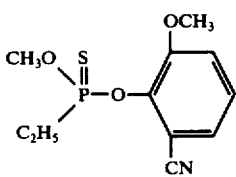

0,0-dimethyl-O-(2-cyano-6-methoxyphenyl) phosphonothioate.

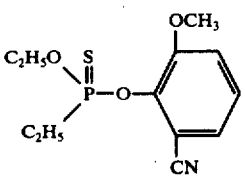

O-ethyl-O-(2-cyano-6-methoxyphenyl) ethylphosphonothioate

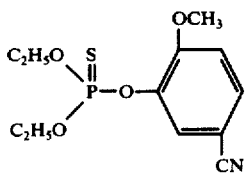

0,0-diethyl-O-(2-methoxy-5-cyanophenyl) phosphorothioate

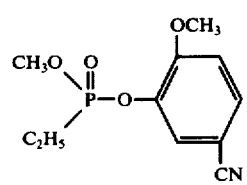

O-methyl-O-(2-methoxy-5-cyanophenyl) ethylphosphonate.

The aforesaid compounds have been tested as pesticides by the following methods:

Adult houseflies and nymphs of the American cockroach and milkweed bug are caged in cardboard mailing tubes with cellophane bottoms and coarse mesh nylon tops and supplied with food and water. From 10 to 25 insects are employed per cage, depending on the species.

The candidate compounds are dissolved in 10 ml. of a suitable solvent, usually acetone. Aliquots of the toxicant solutions are suspended in water containing 0.0175% by volume Sponto 221, an emulsifying agent, and sprayed on the caged insects. The compounds are sprayed with a DeVilbias handsprayer at 20 psi in a fume hood. Final mortality readings are taken after 72 hours. The two-spotted mite, *Tetranychus telarius* (Linn.) is screened by using young pinto bean plants in the primary leaf stage as the host plant. The plant is dipped in an aqueous suspension of the candidate compound and the soil is drenched at a concentration of 100 ppm. based on the weight of the soil. Mites are confined to the leaves with small clip cages. Pesticidal activity is illustrated in the following table, wherein the percentage kill among a group of test species is reported for a specified percentage concentration of toxicant in aqueous solution. A slanted line is used to separate the percentage kill, shown on the left, and the percentage concentration, shown on the right. The pest species tested are as follows:

| House fly | -*Musca domestica* (Linn). |
| American chockroach | -*Paraplanets americana* (Linn.) |
| Spotted milkweed bug | -*Oncopeltus faciatus* (Dallas) |
| Two-spotted mite | -*Tetramychus telarius* (Linn.) |

TABLE I

| | Compound (Example No.) | | | | | |
| --- | --- | --- | --- | --- | --- | --- |
| | 2 % kill/conc. | 5 % kill/conc. | 6 % kill/conc. | 8 % kill/conc. | 10 % kill/conc. | 13 % kill/conc. |
| House Flies | 100/0.1 | 100/0.1 | 100/0.1 | 100/0.1 | 100/0.1 | 100/0.1 |
| American Cockroach | 80/0.05 | 100/0.01 | 100/0.01 | 40/0.005 | 60/0.05 | — |
| Millweed Bug | 90/0.01 | 100/0.01 | 100/0.01 | 100/0.05 | 80/0.05 | 50/0.003 |
| Two-spotted Mite | 50/0.1 | 25/0.1 | 100/0.01 | 100/0.05 | — | 50/0.001 |

The compounds of Examples 2, 5, 6, 8 and 13, which showed high activity against insects, were bioasssayed on the house fly according to the following procedure: Cages such as those described for the insecticide screening tests above were used. Acetone solutions of the candidate materials were prepared and measured aliquots were placed in pyrex Petri dishes having a surface area of 18.8 sq. ccm. One ml. of a suspension of peanut oil and acetone was added as a filming agent. The solvent was evaporated by air-drying and groups of 25 female flies, 3 to 5 days old, were exposed to the residues on the Petri dishes which were placed in the cages. Final mortality readings were taken 48 hours after initiation of the test.

The results of these tests are presented in the following table wherein the percentage kill is shown on the left of the slanted line, and the amount of toxicant is shown on the right.

TABLE II

| Compound (Example No.) | % kill/ g. | % kill/ g. | % kill/ g. |
|---|---|---|---|
| 2 | 96/5 | 4/1 | |
| 5 | 100/10 | 68/5 | 8/1 |
| 6 | 100/10 | 88/5 | 8/1 |
| 8 | 100/5 | 0/1 | |
| 13 | 100/10 | 92/2.5 | 4/1 |

Compound number 5 and compound number 13 exhibited unusual activity against lygus bug (*Lygus hesperus* (Knight)). Compound number 5 has an LD-50 value of 0.0008 percent toward lygus bug and compound number 13 has an LD-50 value of 0.0003 percent.

Where used herein, the term "pesticide" is intended in the restricted sense generally recognized in the art as applying to the lower forms of life customarily controlled by chemical means and excluding the higher animals, the vertabrates, e.g., rodents, birds, and larger forms which are more commonly controlled by mechanical means, such as traps. It will, however, be apparent to one skilled in the art that the toxic activity of the new compounds with various pest species is indicative of activity with species and orders not specifically shown.

Although the above pesticidal tests were accomplished with aqueous dispersions, the toxic compounds may also be used in the form of solutions (aqueous) when appreciably water-soluble, non-aqueous solutions, wettable powders, vapors, and dusts, as may be best suited to the conditions of use.

I claim:

1. A method for killing insects which comprises contacting the insects with an insecticidal amount of at least one compound represented by the formula:

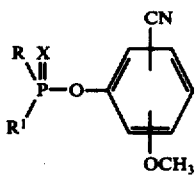

where R and R¹ are members independently selected from the group consisting of lower alkyl, chloro-substituted lower alkyl, lower alkoxy, phenyl, and phenoxy; and X is a member selected from the group consisting of oxygen and sulfur.

2. A method for killing insects which comprises contacting the insects with an insecticidal amount of at least one compound represented by the formula:

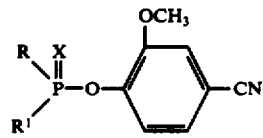

wherein R and R¹ are members independently selected from the group consisting of lower alkyl, chloro-substituted lower alkyl, lower alkoxy, phenyl, and phenoxy; and X is a member selected from the group consisting of oxygen and sulfur.

3. A method for killing insects which comprises contacting the insects with an insecticidal amount of at least one compound represented by the formula:

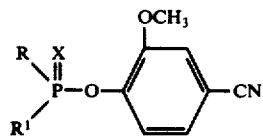

wherein R and R¹ are independently selected lower alkoxy groups and X is selected from the group consisting of oxygen and sulfur.

4. The method for killing insects according to claim 3 wherein R is butoxy, R¹ is butoxy and X is oxygen.

5. The method for killing insects according to claim 3 wherein R is ethoxy, R¹ is ethoxy and K is sulfur.

6. A method for killing insects which comprises contacting the insects with an insecticidal amount of at least one compound represented by the formula:

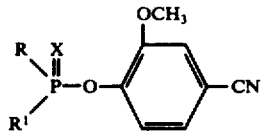

wherein R is lower alkoxy, R¹ is lower alkyl and X is selected from the group consisting of oxygen and sulfur.

7. The method of killing insects according to claim 6 wherein R is ethoxy, R¹ is ethyl and R is sulfur.

* * * * *